(12) United States Patent
Hancock et al.

(10) Patent No.: US 6,809,230 B2
(45) Date of Patent: Oct. 26, 2004

(54) WATERPROOF VENIPUNCTURE SITE COVER

(76) Inventors: Betty Hancock, P.O. Box 45, Rustburg, VA (US) 24588; Patricia Carr, 2155 Volens Rd., Nathalie, VA (US) 24577

(*) Notice: Subject to any disclaimer, the term of this patent is extended or adjusted under 35 U.S.C. 154(b) by 43 days.

(21) Appl. No.: 10/422,278

(22) Filed: Apr. 24, 2003

(65) Prior Publication Data

US 2003/0225377 A1 Dec. 4, 2003

Related U.S. Application Data

(60) Provisional application No. 60/385,066, filed on Jun. 4, 2002.

(51) Int. Cl.$^7$ .............................. A61F 13/00; A61M 5/32
(52) U.S. Cl. .............................. 602/42; 602/54; 602/57; 604/174; 604/179; 604/180
(58) Field of Search ................................ D24/189, 128; 128/878, 879, 881, 882; 602/41, 42, 3, 52, 54, 57; 604/174, 179, 180

(56) References Cited

U.S. PATENT DOCUMENTS

| | | |
|---|---|---|
| 3,194,235 A | 7/1965 | Cooke |
| 4,059,105 A | 11/1977 | Cutruzzula et al. |
| 4,250,882 A | 2/1981 | Adair |
| 4,517,971 A | 5/1985 | Sorbonne |
| 4,743,232 A * | 5/1988 | Kruger ........................ 604/180 |
| 4,846,807 A | 7/1989 | Safadago |
| 5,074,847 A | 12/1991 | Greenwell et al. |
| 5,112,313 A | 5/1992 | Sallee |
| 5,116,324 A | 5/1992 | Brierley et al. |
| 5,397,639 A * | 3/1995 | Tollini ......................... 428/343 |
| 5,449,340 A * | 9/1995 | Tollini ........................... 602/58 |
| 5,707,348 A * | 1/1998 | Krogh ........................... 602/41 |
| 5,885,254 A * | 3/1999 | Matyas ........................ 604/180 |
| 6,117,111 A * | 9/2000 | Fleischmann ................ 604/180 |
| 6,124,521 A * | 9/2000 | Roberts ........................ 602/54 |
| 6,132,399 A * | 10/2000 | Shultz ......................... 604/174 |
| 6,222,090 B1 * | 4/2001 | Weston ......................... 602/41 |
| 2003/0216694 A1 * | 11/2003 | Tollini ......................... 604/174 |

* cited by examiner

*Primary Examiner*—Kim M. Lewis
(74) *Attorney, Agent, or Firm*—Woods, Rogers, PLC; Peter E. Rosden

(57) ABSTRACT

A transparent cover for a venipuncture site providing a transparent window to view the status of the catheter, skin and puncture site and to protect that site from exposure to water, germs and other contaminants. The cover is comprised of one piece of flexible transparent material which conforms to the contour of the skin and has a main body foldably attached to an arm. The arm is adhesively attached behind the catheter to the skin, while the main body is folded on top of the arm and adhesively attached on one side to the arm and to the catheter lying on top of the arm and on its other sides to the skin. A method for applying and removing the cover is also disclosed.

12 Claims, 4 Drawing Sheets

WATERPROOF VENIPUNCTURE SITE COVER

CROSS-REFERENCES TO RELATED APPLICATIONS

The present application claims the benefit of the earlier filing date of U.S. Provisional Patent Application Ser. No. 60/385,066, filed Jun. 4, 2002, which is incorporated by reference herein in its entirety.

TECHNICAL FIELD

The subject invention relates generally to a medical device used in intravenous procedures. The device is particularly useful in providing convenient, self-contained, physical, viral and bacteriological protection to a venipuncture site.

BACKGROUND OF THE INVENTION

The need to protect intravenous infusion sites has long been recognized. Such sites should be disturbed as little as possible both to maximize patient comfort and to minimize the risk of infection or contamination. Venipuncture sites on patients are generally covered with gauze, tape or sealer, and, when a shower or bath is taken, bags or plastic are secured over the site with tape or other adhesives. Catheters secured at such intravenous sites by methods known in the art are often easily dislodged as well as being open to infection due to exposure to water and airborne contaminants. Furthermore, it is necessary to replace existing PRN (pro re nata, or, as needed) adapters as frequently as every 3 days pursuant to hospital protocols. Such adapters may be applied to a catheter when continuous IV fluids are not in use to allow flushing and meds to be given intravenously. Some adapters are even available which permit a needleless system to be used. Thus, the venipuncture cover of the present invention may be used with any system. When PRN adapters are used, dressings around intravenous sites must be taped, often repeatedly, causing great patient discomfort and increasing the risk of dislodging the catheter and allowing infection. Intravenous sites on the back of a hand are sometimes covered with gloves for protection in showers or baths, but the difficulties in waterproofing the glove opening at the wrist also increases the risk of infection from waterborne or airborne contaminants.

Devices for shielding venipuncture sites and for immobilizing cannulae post insertion are generally known in the art. Some of these devices include transparent portions for observing their status and functioning. Others include hinged mechanisms to facilitate direct access to the venipuncture site ostensibly without irritating the patient's skin by the removal and replacement of adhesive tape. Still others use complicated multilayered structures to prevent and detect exposure to moisture There are even additional, separate devices which are designed to be used in conjunction with venipuncture shields just to protect those sites while the patient showers or bathes. However, despite their improvements, many of these devices are clumsy to use, unnecessarily bulky, expensive or require chemical additives or coatings to function properly.

Therefore, there remains a need for a simple, self-contained, inexpensive, nonbulky venipuncture cover device that substantially eliminates patient discomfort when needles are changed, is transparent to permit monitoring, eliminates the need for the additional application of tape, provides an extended wearing period without the need for replacement and does not require the use of additional mechanisms or safety measures when a patient wishes to bathe or shower.

SUMMARY OF THE INVENTION

This invention relates to a venipuncture cover for catheters at intravenous sites of patients undergoing medical treatment. The cover is made in one piece from a flat, transparent, flexible, nonbiocompatible material and has two primary parts. The first part is a main body which may have a generally rectangular shape and includes a tab on one side thereof. An adhesive is placed around the periphery of the interior surface of the main body, except for the tab, which is then covered by a protective, removable sheet. The second part is an arm which is foldably connected to the end of a side of the main body opposing the side on which the tab of the main body is located. The arm terminates in a tab. The width of the arm and the width of the main body are substantially the same. Both the interior and exterior surfaces of the arm, except for the arm's tab, are coated with an adhesive and are covered by protective, removable sheets. After removal of the protective sheets, the exterior surface of the arm is adhesively affixed to the skin of a patient behind and beneath the catheter in proximity to the intravenous site. A waterproof, contamination barrier is provided by the cover after the protective sheets are removed from the interior surfaces of the main body and the arm and those two surfaces are adhesively sealed to each other along one side of the main body while the other three sides of the main body are similarly sealed to the skin of the patient.

It is a primary objective of this invention to provide a self-contained cover for a venipuncture site which provides protection from bacteria, moisture, infection, and airborne or waterborne contaminants.

An additional objective of this invention is to provide a cover for a venipuncture site which permits easy removal after intravenous treatment is completed.

Another objective of this invention is to provide a cover for a venipuncture site which enables a patient or user to complete normal personal hygiene functions without risk of disturbance and the necessity to add further protective material to the cover.

It is a further objective of this invention to provide a cover for a venipuncture site which is substantially transparent thereby enabling medical personnel to visually examine the puncture site without removing the cover and to monitor that site for leakage, swelling, irritation and infection.

It is yet another objective of this invention to provide a cover for a venipuncture site which is clear and flexible.

It is still another objective of this invention to provide a cover for a venipuncture site which is a one-part device and can thus be more easily and inexpensively manufactured, packaged and transported.

Yet an additional objective of this invention is to provide a cover for a venipuncture site which permits the patient or user to be more functionally independent than other such covers known in the art.

It is another objective of this invention to provide a venipuncture cover which optionally allows easy, painless periodic changing of the PRN adapter.

Another objective of this invention is to provide a venipuncture cover which can remain in place for up to at least three days or in conformance with any hospital protocols in use.

A further objective of this invention is to provide nurses and others charged with establishing venipuncture sites with the option of securing either the PRN adapter or the cannula to the cover and the skin when setting up such sites.

Yet another objective of this invention is to provide a venipuncture cover which is flexible enough to easily conform to the contours of any anatomical position where it is placed while being adhesively retained in that position.

Yet a further objective of this invention is to provide is to extend the comfortable and safe period during which a venipuncture cover may remain in place without being replaced.

BRIEF DESCRIPTION OF THE DRAWINGS

The foregoing and other objects, aspects and advantages of the invention will be better understood from the following detailed description of the invention with reference to the drawings, in which.

DETAILED DESCRIPTION OF THE INVENTION

Figure 1:
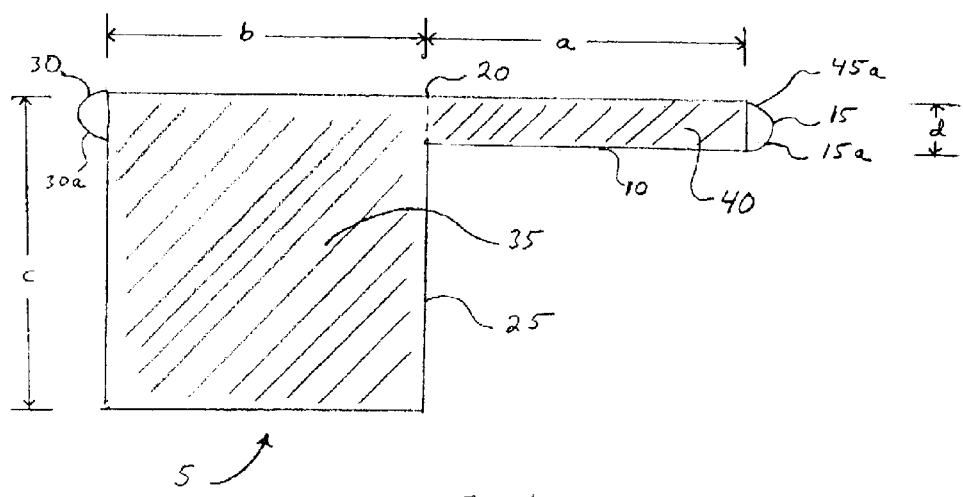
FIG. 1 is an overhead view of the interior surface of the venipuncture cover of the invention in an open position

For a more detailed understanding of the invention, reference is first made to FIG. 1 of the drawings. This figure illustrates an overhead view of the interior surface of venipuncture cover 5 of the present invention which is comprised of a single, substantially flat sheet of a flexible, waterproof, transparent, nonbiocompatible material such as Tegaderm®, a registered trademark of Minnesota Mining and Manufacturing Company. Cover 5 has a narrow, generally flat, two-sided arm 10 with a tab 15 at one end thereof connected along a foldable hinge line 20 to main body 25 of cover 5. Arm 10 may be connected on either the right or the left side of main body 25, as desired. A nonbiocompatible material for the purposes of use in and with cover 5 is one which is not absorbed or degraded when it comes into contact with biological material such as skin and yet does not have a toxic, injurious or immunological response when placed in contact with living tissue. Line 20 may be formed in any of a number of ways, for example, by weakening or perforating the material of which cover 5 is made along line 20. The width "a" of arm 10 should be equal to the width "b" of body 25. Body 25 also includes a tab 30. The tabs 15 and 30 depicted in FIG. 1 are approximately semi-circular in shape, but any shape is acceptable so long as the tab is amenable to grasping as explained below. Furthermore, tab 30 may be located at any point along the side of the main body opposite to the side foldably connected to arm 10. A removable protective sheet 35 covers all of body 25 except for tab 30, while arm 10 is covered by a separate removable sheet 40 extending from hinge 20 to the beginning of tab 15 which remains uncovered. Alternatively, arm 10 and body 25 may be covered by a single removable sheet and whichever removable sheets are used may include duplicates 15a and 30a of tabs 15 and 30 to facilitate removal of the removable sheet or sheets as explained below. In still another embodiment, each removable sheet may be replaced by multipart removable sheeting each having two or three pieces for covering the surface of body 25 and arm 10 which pieces may be joined along a line or lines that becomes visible when the interior surface of cover 5 is flexed convexly thereby enabling a user to grasp each sheet and peel it away from cover 5. Such a configuration would eliminate the need for tabs 15a and 30a. In addition a separate removable sheet 45, not visible in FIG. 1, covers the opposing, exterior side of arm 10 and also extends from hinge 20 to the beginning of tab 15. Sheet 45 preferably also includes tab 45a, which is a duplicate of tab 15, to facilitate its removal, although tab 45a may also be dispensed with in the event a multipart sheet with a dividing line which becomes exposed upon convexly flexing the exterior surface of cover 5 is used. Cover 5 may be made in a variety of sizes and shapes as needed and suitable for use at particular anatomical locations. For example, in a typical use on the arm of a patient, body 25 of cover 5 could be a square with a length "c" of 5 cm. and a width "b" of 5 cm., while arm 10 would have a width "a" of 5 cm. and a length "d" of 1 cm. Other dimensions and physical configurations are also possible, although length "d" of arm 10 is preferably 2 cm or less. In addition, the corners and sides of cover 5 may be curved to enhance patient comfort and ease of removal. The thickness of the material from which cover 5 is made is immaterial so long as it remains flexible and is suitable to carry out the functions attributed to cover 5 herein. Clearly, if the material becomes too thick, for example in excess of 0.5 millimeter, it will become relatively inflexible, and, hence, both less able to conform to the contours of the skin surface to which it must adhere and inherently resistant to the attempts of the adhesive with which it is partially coated to keep it in place over a skin surface which may not be flat.

Figure 2:
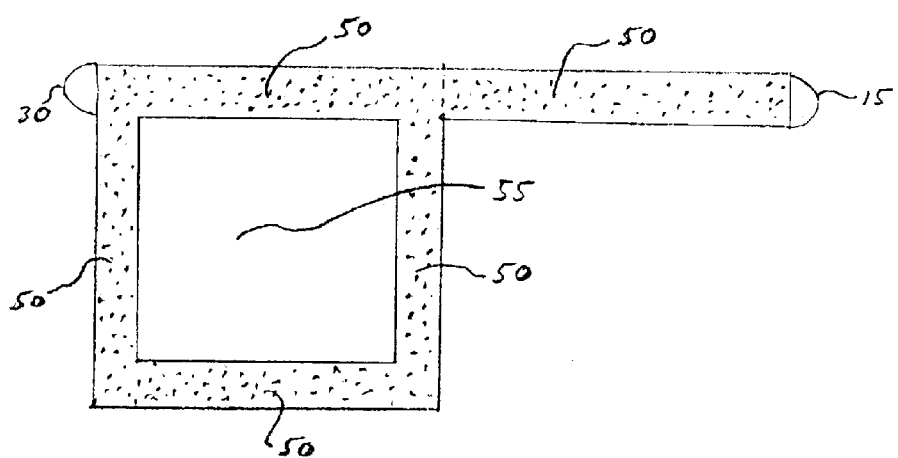
FIG. 2 is an overhead view of the interior surface of the venipuncture cover of the invention in an open position with surface protecting sheets removed.

Sheets 35, 40 and 45 maintain the sanitary, germ-free condition of cover 5 prior to its use as well as preserving and protecting the adhesive coating on cover 5 which is described below with regard to FIG. 2. These sheets may be removed by grasping tabs 15a, 30a and 45a and peeling the respective protective sheets away from cover 5. Alternatively, if no tabs 15a and 30a are included, the multipart protective sheet described above maybe used or a fingernail may be inserted between the respective protective sheet and cover 5 in order to loosen and lift the sheet sufficiently to grasp it and pull it off. FIG. 2 shows an overhead view of the interior surface of venipuncture cover 5 after protective sheets 35 and 40 have been removed. The speckled areas 50 around the periphery of body 25 and along the entire width of arm 10 indicates the presence of a nonbiocompatible, waterproof, airproof adhesive material of a type known in the art which has been applied to cover or coat the respective shaded surfaces during or after the process of manufacturing cover 5. The shaded area around the periphery of body 25 may be any desired width so long as a sufficient area is left uncoated in the center of body 25 to permit unrestricted and undistorted viewing of the venipuncture site after cover 5 is situated. In most cases, a width of between about 0.5 cm and 1.5 cm will be sufficient. The opposing exterior side of arm 10 which is not visible in FIG. 2 is also coated with the same biocompatible adhesive material which becomes exposed upon removal of sheet 45. Note that tabs 15 and 30 are not covered by the adhesive material so that they remain accessible for eventually removing cover 5 from contact with the patient's skin. The center section 55 of body 25 remains transparent after sheet 35 is removed.

In order to create a venipuncture site, typically a needle extending from within a cannula is inserted into the desired area of a patient's anatomy until a vein is entered. Then, the cannula is moved forward along the needle until it too enters the vein and the needle is removed. Thereafter, a PRN adapter is placed at the end of the cannula somewhat above the point where it projects out of the patient's skin into open air. The PRN adapter is present for use as needed and is required for flushing out the cannula. The exposed cannula and an area of skin surrounding the insertion point are then covered by a dressing. The dressing, cannula and adapter must usually be changed at least every three days as a result of exposure to moisture due to personal hygiene requirements of the patient or general contamination of the site. Such frequent changes are physically uncomfortable for the patient and create topical skin irritation which may eventually become so severe as to require relocation of the cannula and dressing to other sites. As explained below, by using cover 5, securing of the cannula and PRN adapter becomes a quick and easy process which, when completed, provides the venipuncture site with a waterproof barrier, protection from bacteriological, contaminant and viral exposure and a transparent window through which the status of the site can be monitored.

After a venipuncture site has been chosen and the cannula situated, a person, such as a nurse, removes cover 5 from the protective packaging, typically a tearable paper pouch, in which it is stored. After unfolding body 25 away from arm 10, sheet 45 is removed by grasping tab 45a and peeling sheet 45 away from arm 10. Sheet 40 may then be removed by grasping tab 15a and peeling sheet 40 away from arm 10. The responsible person then holds cover 5 by grasping body 25 between sheet 35 which still covers body 25 from both sides of cover 5 with the fingers of one hand, positions arm 10 so that it extends behind the catheter tube leading to the skin puncture point and holds nonadhesive covered tab 15 between the fingers of the other hand. Alternatively, sheets 45 and 40 may be removed after positioning arm 10 behind the catheter tube leading to the skin puncture point depending on the convenience of the user. In both cases, arm 10 is pulled relatively taut between the two hands and slid under the portion of the cannula protruding above the skin but without touching the skin. It is then optional with the user whether to adhesively affix arm 10 to the skin directly below the PRN adapter or to affix it at a point beyond the PRN adapter and closer to the skin entry area. Preferably, arm 10 is situated below the PRN adapter in order to protect the access area where the cannula penetrates the skin.

Figure 3:
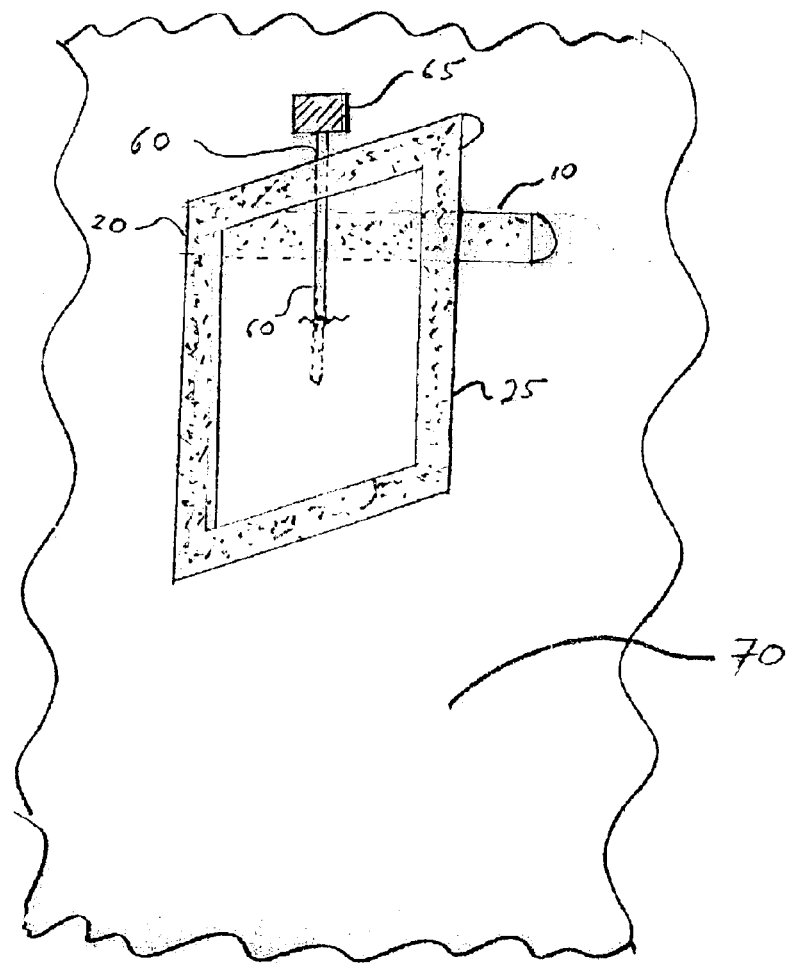
FIG. 3 is a perspective overhead view of the venipuncture cover of the invention after partial attachment to the skin of a patient.

Regardless, arm 10 is adhesively affixed to the skin at the chosen site. Sheet 35 is then removed from body 25 by grasping tab 30a and peeling sheet 35 away until it is separated from body 25 and the adhesive areas around the periphery of body 25 are exposed. After folding body 25 along fold line 20, the adhesive portion of body 25 opposing arm 10 is brought into physical abutment with the adhesive-coated exposed area of arm 10 so that tab 30 overlaps tab 15, and light pressure is applied along the length of body 25 onto arm 10 to seal one side of body 25 to arm 10 and around the cannula. FIG. 3 is a perspective view of cover 5 after cannula 60 with PRN adapter 65 has been inserted into the skin 70 of a patient, arm 10 has been affixed to the skin of the patient beneath cannula 60 and body 25 has been folded along fold line 20. Thereafter, the other three sides of body 25 are similarly brought into physical contact with the patient's skin and sealed in place by the exertion of light pressure onto the exterior surface of each edge either simultaneously together or individually, as preferred. When attaching these three sides of body 25, care should be taken not to place those sides in a manner that results in body 25 being in such tight contact with the skin that it places undesirable pressure on the cannula. Such excessive pressure may damage the proper functioning of the cannula and/or may cause pain to the patient. An alternative configuration for body 25 would provide flat peripheral areas 50 to accept the application of an adhesive coating, while center section 55 would include a slight excess of the material from which cover 5 is made so as to form a pouch-like structure. In this way, less care would have to be taken when positioning areas 50 to avoid exerting excessive pressure on the cannula or insertion area in the skin although attention would still have to be paid to the pressure exerted when adhering body 25 to arm 10.

Figure 4:
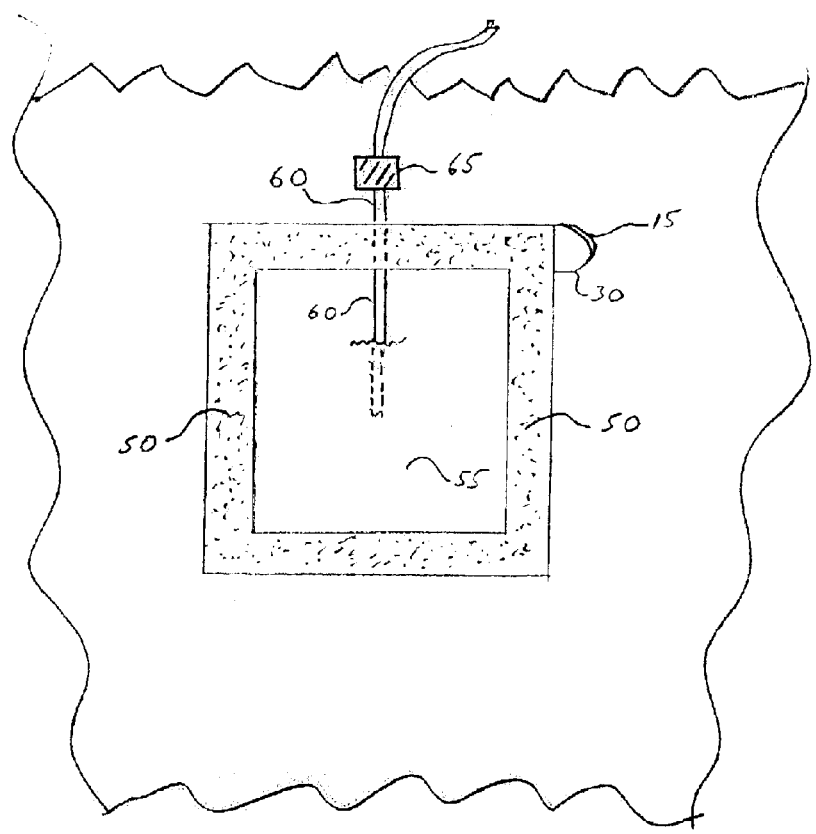
FIG. 4 is an overhead view of the venipuncture cover of the invention after it has been finally placed in position on the skin of a patient.

FIG. 4 is an overhead view of cover 5 and a cannula after both have been placed in position on a patient and the venipuncture site has been sealed underneath cover 5. The speckled areas 50 around the periphery of body 25 correspond to the areas to which an adhesive coating or covering has been applied as described above. Note that the center of body 25 is essentially transparent so that the end of cannula 60 protruding above the skin and the entire venipuncture site is clearly visible and may, as a result, be monitored at will. Furthermore, no covering or protective sheet need be applied to the exterior surface of body 25 since that surface does not come into contact with the patient's skin. In an alternative embodiment, such a cover could be applied, if desired, for example when the cover is used in a surgical theater where a higher level of sterility is desired than would be available in an open air environment.

When in place, the one-piece venipuncture cover of this invention protects the puncture site from moisture, bacteria and other types of contamination. In addition, due to the waterproof seal provided, it enables the patient to bathe or shower while continuing to receive medication, hydration or blood. Furthermore, cover 5 provides a tight seal above and below cannula 60 without the need for using any irritating surgical tape and is not easily dislodged by involuntary contact, making the cannula itself more secure and avoiding the patient discomfort otherwise caused by taping and retaping of dressings. Finally, the unibody structure of cover 5 out of a single material with only adhesive coatings shielded by protective sheets added thereto makes cover 5 particularly simple and inexpensive to manufacture and use.

Eventually, it usually becomes necessary to change a venipuncture site dressing either because a vein has collapsed, the site has become irritated or infected or the patient has inadvertently or intentionally removed the IV access. Cover 5 is uniquely suited to such a requirement. When it must be removed, tab 30, which overlaps tab 15 when cover 5 is in place, may be individually grasped between a user's fingers and peeled back to separate body 25 from both the skin and from arm 10. Then, cannula 60 can be removed. Thereafter, tab 15 is grasped and pulled away from adhesive contact with the skin freeing cover 5 for disposal as waste material.

Although various elements in the previously described embodiments of this invention have been disclosed with reference to particular types of materials and particular sequences of steps, it should be understood that the functions performed by these materials may also be performed in appropriate cases by other types of materials and that this invention is not limited by reference to the specific materials disclosed. Furthermore, the process steps disclosed are not the only way in which the function of this invention can be implemented Other embodiments and sequences of steps are possible so long as the overall structure, method and advantages described above are preserved.

What is claimed is:

1. A removable venipuncture cover for a dermatological surface made from a substantially transparent, one-piece, nonbiocompatible material having an interior and an exterior surface wherein the cover is generally flat, self-contained and flexible comprised of:

a main body with a generally rectangular shape including a first tab at one corner thereof wherein a nonbiocompatible, waterproof, airproof adhesive material has been applied in a predetermined width along the periphery of the interior surface thereof, excluding the first tab, and wherein further the interior surface thereof is covered by a removable sheet duplicating the size and shape of said main body; and an arm with a generally rectangular shape foldably attached along one edge of its length to said main body at one corner of said main body wherein the opposing side of its length includes a second tab, said arm having a width generally equally to the width of said main body wherein a nonbiocompatible adhesive material has been applied across the entire interior and exterior surfaces of said arm, excluding the second tab, and wherein further both the interior and exterior surfaces of said arm are covered by separate, removable sheets duplicating the size and shape of said arm.

2. The cover of claim 1, wherein the removable sheets covering said main body and said are multipart removable sheets joined along lines which become visible upon flexing and which do not include tabs.

3. The cover of claim 1, wherein the thickness of the material from which the cover is made is 0.5 mm or less.

4. The cover of claim 1, wherein the cover is flexible enough to conform to and assume the shape of the dermatological contour against which it is placed.

5. The cover of claim 1, wherein the length of said arm is 2 cm. or less.

6. The cover of claim 1, wherein the corners of said main body are rounded.

7. The cover of claim 1, wherein the predetermined width of the adhesive applied along the periphery of said main body is between 0.5 cm and 1.5 cm.

8. The cover of claim 1, wherein an excess of material sufficient to form a pouch-like structure is included in the central area of said main body.

9. The cover of claim 1, wherein said main body further includes a removable sheet duplicating the size and shape of said main body covering the exterior surface of said main body.

10. A method for applying a folded, removable, one-piece venipuncture cover to a dermatological intravenous site where a catheter and a PRN adapter are situated wherein the venipuncture cover is made from a generally flat, flexible, substantially transparent, nonbiocompatible material having an interior and exterior surface and wherein further the cover includes a generally rectangular main body having a first tab with an adhesive applied to the periphery of the interior surface thereof, excluding the tab, which interior surface is covered by at least one removable sheet and a generally rectangular arm foldably attached on one side of its length along a predetermined fold line to the main body and terminating on the other side of its length in a second tab, both the interior and exterior surfaces of the arm, except for the tab, being coated with an adhesive and covered by at least one removable sheet, comprising:

unfolding the main body from the arm;

removing the removable sheets from the exterior and interior surfaces of the arm;

grasping the main body with the fingers of one hand and the second tab of the arm with the fingers of the other hand behind the catheter and above the skin;

drawing the arm relatively taut;

moving the arm beneath the catheter to a point where it is desired to adhesively affix it to the skin;

placing the exterior, adhesively coated surface of the arm into contact with the skin;

detaching the removable sheet from the interior surface of the main body;

folding the main body along the fold line on top of the arm;

exerting light pressure along the periphery of the main body so as to form an adhesive seal between the main body and the arm along one side and between the main body and the skin along the other three sides.

11. A method for removing a folded, removable, one-piece venipuncture cover from a dermatological intravenous site where a catheter and a PRN adapter are situated wherein the venipuncture cover is made from a generally flat, flexible, substantially transparent, nonbiocompatible material having an interior and exterior surface and wherein further the cover includes a generally rectangular main body having a first tab with an adhesive applied to the periphery of the interior surface thereof, excluding the tab, and a generally rectangular arm foldably attached on one side of its length along a predetermined fold line to the main body and terminating on the other side of its length in a second tab, both the interior and exterior surfaces of the arm, except for the tab, being coated with an adhesive, the arm being adhesively attached on its exterior surface to the dermatological site and the main body being adhesively attached on one side of the periphery of its interior surface to the interior surface of the arm and on the other three sides of the periphery of its interior surface to the dermatological site, comprising:

grasping the first tab with the fingers of one hand;

peeling back the main body from adhesive contact with the skin while unfolding it away from the arm;

removing the catheter and PRN adapter;

further grasping the second tab with the fingers of one hand; and further peeling back the arm from adhesive contact with the skin.

12. A removable venipuncture cover for a dermatological surface made from a substantially transparent, one-piece, nonbiocompatible material having an interior and an exterior surface wherein the cover is generally flat, self-contained and flexible comprised of:

a main body with a generally rectangular shape including a first tab at one corner thereof wherein a nonbiocompatible, waterproof, airproof adhesive material has been applied in a predetermined width along the periphery of the interior surface thereof, excluding the first tab;

an arm with a generally rectangular shape foldably attached along one edge of its length to said main body at one corner of said main body wherein the opposing side of its length includes a second tab, said arm having a width generally equally to the width of said main body wherein a nonbiocompatible adhesive material has been applied across the entire interior and exterior surfaces of said arm, excluding the second tab;

a first removable sheet covering both the interior surface of said main body and the interior surface of said arm; and a second removable sheet covering the exterior surface of said arm.

* * * * *